United States Patent [19]

Barberet et al.

[11] Patent Number: Plant 6,277

[45] Date of Patent: Sep. 6, 1988

[54] CARNATION NAMED 'LONBEREC'

[75] Inventors: Nicole Barberet; Yves Ducloux, both of Antibes, France

[73] Assignee: Laboratoire de Physiologie Vegetale de la Londe, La Londe, France

[21] Appl. No.: 906,541

[22] Filed: Sep. 13, 1986

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new carnation cultivar having bright red blooms produced profusely at intermittent intervals of spring, midseason and fall. The flowers are of medium size and are borne singly on a strong, erect stem, the flowers being distinguished by the strong cardinal red color of the petals and the plant itself being distinguished by its medium growth and vigorous, upright and very rigid habit with moderately abundant foliage.

1 Drawing Sheet

BACKGROUND OF THE NEW PLANT

This new carnation variety originated as a seedling resulting from our crossing of plants selected from our collection of carnations maintained for breeding purposes at La Londe, Les Maures, France. Our object in making this crossing was to develop a commercial carnation having blooms of good quality and nice color on a strong plant having resistance to *Fusarium oxysporum*. Since 1983, this plant has been reproduced by cuttings with very good results so that further propagation has been carried on through a series of successive generations by means of cuttings from previous plants produced in the same manner. This extended propagation of our new seedling demonstrated clearly that the novel characteristics of its blooming and growth habits would remain true from generation to generation and appeared to be firmly fixed.

DESCRIPTION OF THE DRAWING

Our new variety of carnation is illustrated by the accompanying photographic drawing, which shows in full color a typical arrangement of buds and flowers at various stages of opening, the colors shown being as nearly true to those specified as is reasonably possible to obtain by conventional photographic procedures.

DESCRIPTION OF THE NEW PLANT

The following is a detailed description of our new carnation plant based upon observations of greenhouse plants grown at La Londe, Les Maures, France, in the spring of the year, the color designations being according to The R.H.S. Colour Chart published by The Royal Horticultural Society of London, England.

THE PLANT

Origin: Seedling.

Parentage:

*Seed plant.*—Stock Variety 80 R 70.

*Pollen plant.*—Stock Variety 78 P 10. These parent varieties were selected by us from our collection of breeding plants and each is individually identified in our permanent records maintained in our office at La Londe.

Classification:

*Botanic.*—*Dianthus caryophyllus.*

*Commercial.*—Standard carnation.

Form: Moderate height, erect bush with at least four stems being emitted near the ground.

Main stem:

*Length.*—Less than 15 cm. due to pinching.

Branching character: Rather few branches.

Growth habit: Vigorous, upright and very rigid.

Foliage:

*Quantity.*—Moderately abundant.

*Number of leaves.*—More than 120.

*Size of leaf.*—Leaf averages about 15.2 cm. long and about 7 mm. wide at the seventh node.

*Leaf shape.*—Long with a curved margin.

*Texture.*—Leathery.

*Color.*—Both upper and lower sides, 189A/B.

*Leaflets.*—None.

*Ribs, veins and rachis.*—Hardly noticeable.

THE BUD

Size:

*Diameter.*—Averages about 2.2 cm.

*Length.*—Averages about 2.9 cm.

Shape: Ovoid.

Rate of opening: Normal for carnations.

Color of petals:

*When sepals first divide.*—45C.

*When petals begin to unfurl.*—46C.

Sepals:

*Number.*—About 5.

*Shape.*—Joined together at lower part and having a sharp, pointed apex. The sepals are hooded over the bud before dividing and continue to stand up as the flower opens.

*Color.*—Inside — 139C and 145B. Outside — 145D.

*Striae.*—Longitudinal.

Calyx: Medium size and of funnel shape.

*Aspect.*—Smooth; the calyx rarely splits.

Flower stem:

*Length.*—About 74.2 cm., in average.

*Character.*—Erect and rigid.

*Color.*—189A/B.

THE FLOWER

Blooming habit: Recurrent, blooming profusely during spring, midseason and fall blooming periods with a tendency to give fewer blooms in the fall.

Size of bloom: Medium.

*Diameter.*—Averaging about 7.5 cm.
*Depth.*—Averaging about 5.5 cm.
Borne: Singly.
Shape:
*When bloom first opens.*—Flat.
*When bloom matures.*—Slightly high-centered.
Petalage:
*Number of petals.*—Averaging about 62.
*Arrangement.*—Generally imbricated.
*Petal form.*—Fan shaped with rounded edges and finely serrated apex.
*Texture.*—Leathery.
*Appearance.*—Satiny.
*Color.*—Both outer and inner petals: Body — 46C. Base — Greenish. Reverse side — 45C.
Petaloids: Less than 11.
*Size.*—Smaller than petals.
*Color.*—Same as petals.
Flower stem:
*Length.*—Averaging about 74.2 cm. (cut at the tenth node).
*Character.*—Strong and upright.
*Color.*—189A/B.
Discoloration after full bloom: Lightly darker color.
Fragrance: Perceptible.
Persistence: The flowers hang on and dry.
Lasting quality:
*As cut flower.*—At least ten days in vase keeping.

Disease resistance: Resistant to *Fusarium oxysporum* at La Londe, Les Maures, France.

REPRODUCTION ORGANS

Stamens:
*Number.*—10 to 16.
*Arrangement.*—Around the ovary.
*Anthers.*—Size: About 4 mm. Color: White.
Filaments:
*Length.*—Averages about 2.6 cm.
Pistils:
*Number.*—About 4.
*Styles.*—Length: Averaging about 2.6 cm. Color: Lightly red.
*Stigmas.*—Color: Lightly red.
Ovaries: The ovaries are ribbed.

This new spray carnation variety most nearly resembles the variety 'Ember', an unpatented variety, but differs from that variety by having a more lightly serrated petal, a calyx that splits less, a longer stem and by being resistant to *Fusarium oxysporum.*

We claim:

1. A new and distinctive carnation cultivar, substantially as herein shown and described, characterized by its intermittent flowering habit with profuse production of flowers, having a substantially solid cardinal red coloration, and having a rigid, vigorous and upright growth habit with a normal height of about 108 cm. at eight months.

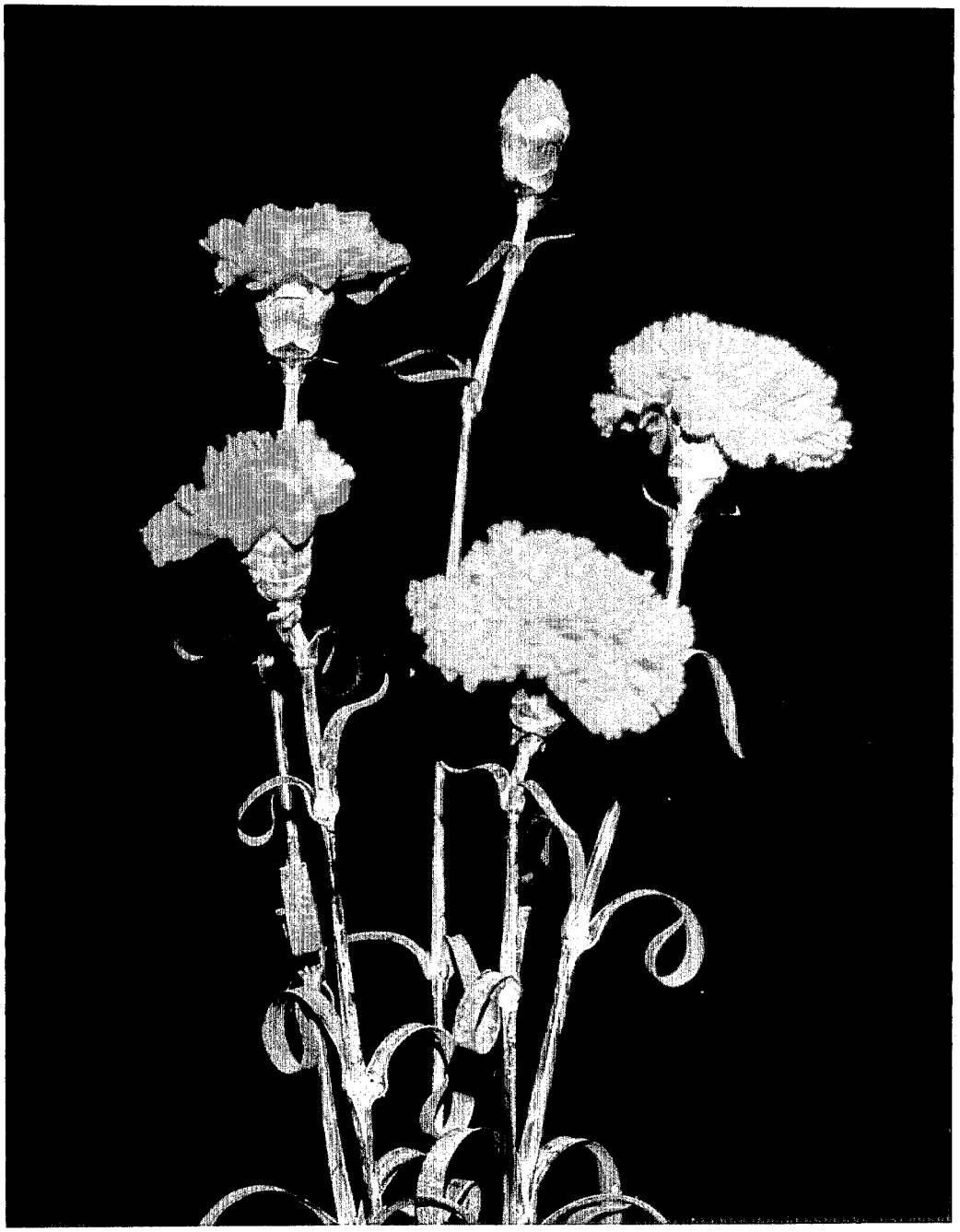

* * * * *